US011389505B2

(12) United States Patent
Kumagai et al.

(10) Patent No.: US 11,389,505 B2
(45) Date of Patent: *Jul. 19, 2022

(54) METHOD OF MANAGING JOINT PAIN

(71) Applicant: ORTHOTROPHIX, INC., Oakland, CA (US)

(72) Inventors: Yoshinari Kumagai, Foster City, CA (US); Dawn McGuire, Orinda, CA (US); Meghan Miller, Antioch, CA (US); David Rosen, Hayward, CA (US)

(73) Assignee: ORTHOTROPHIX, INC., Oakland, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 17/067,278

(22) Filed: Oct. 9, 2020

(65) Prior Publication Data
US 2021/0236595 A1 Aug. 5, 2021

Related U.S. Application Data

(62) Division of application No. 16/006,475, filed on Jun. 12, 2018, now Pat. No. 10,849,957.

(60) Provisional application No. 62/519,538, filed on Jun. 14, 2017.

(51) Int. Cl.
| | | |
|---|---|---|
| *A61K 38/00* | (2006.01) | |
| *A61K 38/16* | (2006.01) | |
| *A61K 47/36* | (2006.01) | |
| *A61K 9/00* | (2006.01) | |
| *A61K 9/19* | (2006.01) | |
| *A61P 19/02* | (2006.01) | |
| *C07K 14/47* | (2006.01) | |
| *A61K 38/17* | (2006.01) | |
| *A61K 31/728* | (2006.01) | |
| *A61B 5/00* | (2006.01) | |

(52) U.S. Cl.
CPC ........ *A61K 38/1709* (2013.01); *A61B 5/4585* (2013.01); *A61K 9/0019* (2013.01); *A61K 9/19* (2013.01); *A61K 31/728* (2013.01); *A61K 38/16* (2013.01); *A61K 47/36* (2013.01); *A61P 19/02* (2018.01); *C07K 14/47* (2013.01); *C07K 14/473* (2013.01); *A61B 5/4824* (2013.01); *A61K 38/00* (2013.01)

(58) Field of Classification Search
CPC .............. A61K 2300/00; A61K 31/728; A61K 38/1709; A61K 38/00; A61K 38/16; A61K 47/36; A61K 9/0019; A61K 9/19; A61K 9/00; C07K 14/001; C07K 14/47; C07K 14/473; C07K 14/00; A61P 19/02
See application file for complete search history.

(56) References Cited

U.S. PATENT DOCUMENTS

| | | |
|---|---|---|
| 7,638,486 B2 | 12/2009 | Lazarov et al. |
| 7,888,462 B2 * | 2/2011 | Middleton-Hardie ...................... A61P 19/02 530/324 |
| 2009/0062201 A1 | 3/2009 | Kumagai et al. |
| 2011/0105401 A1 | 5/2011 | Middleton-Hardie et al. |

FOREIGN PATENT DOCUMENTS

WO   WO 2008/091632   7/2008

OTHER PUBLICATIONS

Knee Injury and Osteoarthritis Outcome Score from https://www.physio-pedia.com/Knee_Injury_and_Osteoarthritis_Outcome_Score, pp. 1-8. Accessed Mar. 29, 2020. (Year: 2020).*
AC-100 from https://www.drugbank.ca/drugs/DB05671, pp. 1-3. Accessed Apr. 4, 2020. (Year: 2020).*
Maheswaran et al. "A Study to Investigate the Osteogenic Potential of Peptide AC-100," EC Orthopaedics, Jan. 31, 2017 (Jan. 31, 2017), vol. 5, Iss. 3, pp. 82-87. Entire Document.
Rowe et al. "MEPE has the properties of an osteoblastic phosphatonin and minhibin," Bone, Nov. 26, 2003 (Nov. 26, 2003), vol. 34, Iss. 2, pp. 303-319. Entire document.
Karsdal M. A. et al., "Disease-modifying treatments for osteoarthritis (DMOADs) of the knee and hip: lessons learned from failures and opportunities for the future", Osteoarthritis and Cartilage, Bailiere Tindall, London, GB, vol. 24, No. 12, Aug. 2, 2016 (Aug. 2, 2016), pp. 2013-2021, XP029806790.
McGuire D. et al., "TPX-100 leads to marked, sustained improvements in subjects with knee osteoarthritis: pre-clinical rationale and results of a controlled clinical trial", Osteoarthritis and Cartilage, vol. 26, Apr. 1, 2018 (Apr. 1, 2018), p. S243, XP055780810, GB.
Walsh David A. et al., "Treating People With Joint Pain", International Association for the study of Pain 2016, Jan. 1, 2016 (Jan. 1, 2016), XP055782164, Retrieved from the Internet: URL: https://s3.amazonaws.com/rdcms-iasp/files/production/public/Content/Contentfolders/GlobalYearAgainstPain2/2016/FactSheets/English/1.%20Patients%20Joint%20Pain.pdf [retrieved Mar. 4, 2021] the whole document.

* cited by examiner

*Primary Examiner* — Julie Ha
(74) *Attorney, Agent, or Firm* — Karl Bozicevic; Bozicevic, Field & Francis LLP

(57) ABSTRACT

A method of alleviating joint pain in a patient comprising evaluating the patient's joint pain when undergoing motions associated stress to the joint, and injecting the patient with a peptide of SEQ ID No. 1, and thereafter evaluating the patient's joint pain when undergoing the same motion.

11 Claims, 12 Drawing Sheets
Specification includes a Sequence Listing.

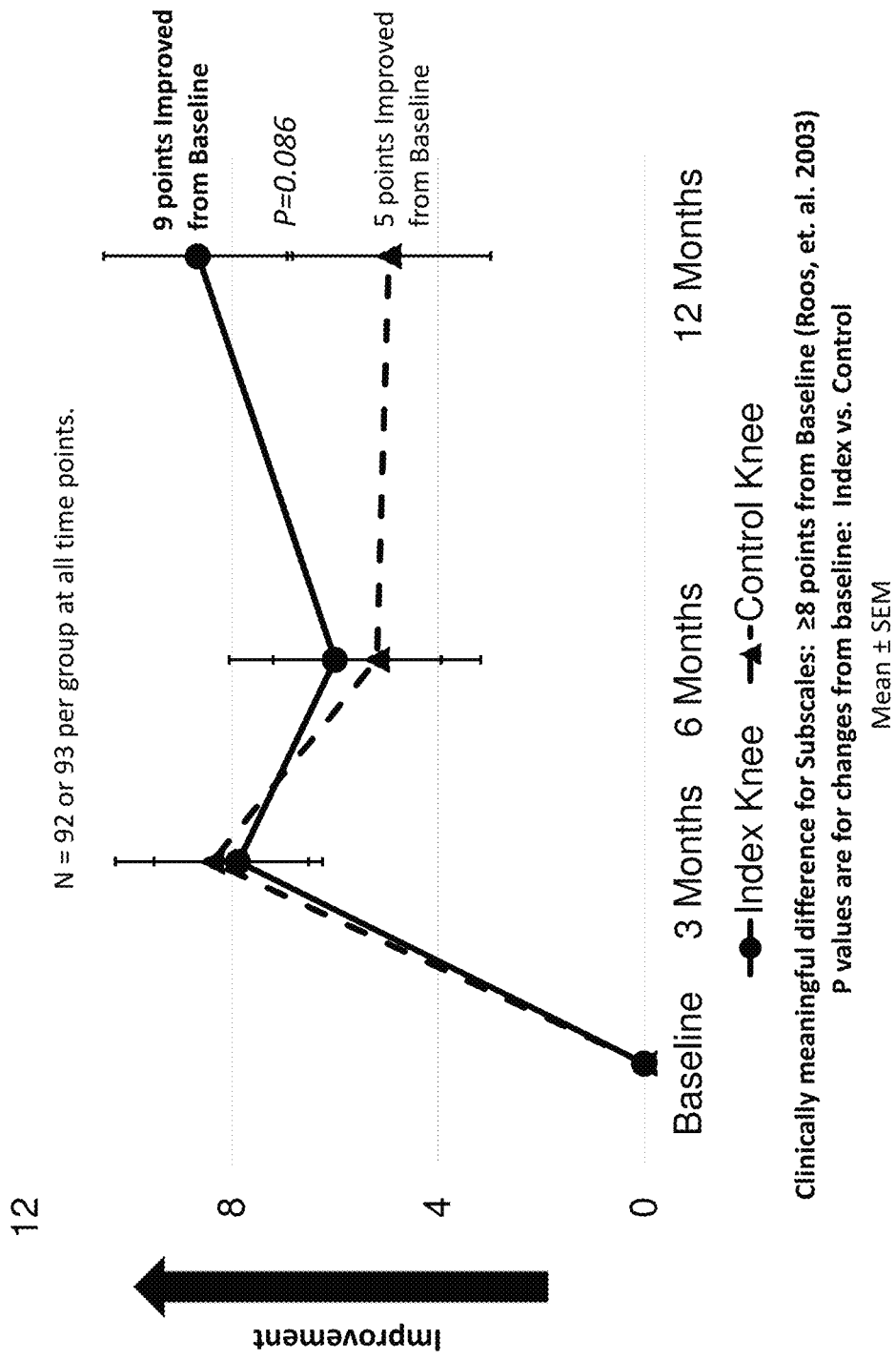

Figure 2: KOOS – Pain Questions

1. How often do you experience RIGHT/LEFT knee pain?

Never (0), Monthly (1), Weekly (2), Daily (3), Always (4)

What amount of RIGHT/LEFT knee pain have you experienced the last week during the following activities?

2. Twisting/pivoting on your knee
3. Straightening knee fully moving
4. Bending knee fully
5. Walking on flat surface
6. Going up or down stairs
7. At night while in bed
8. Sitting or lying
9. Standing upright None (0), Mild (1), Moderate (2), Severe (3), Extreme (4)

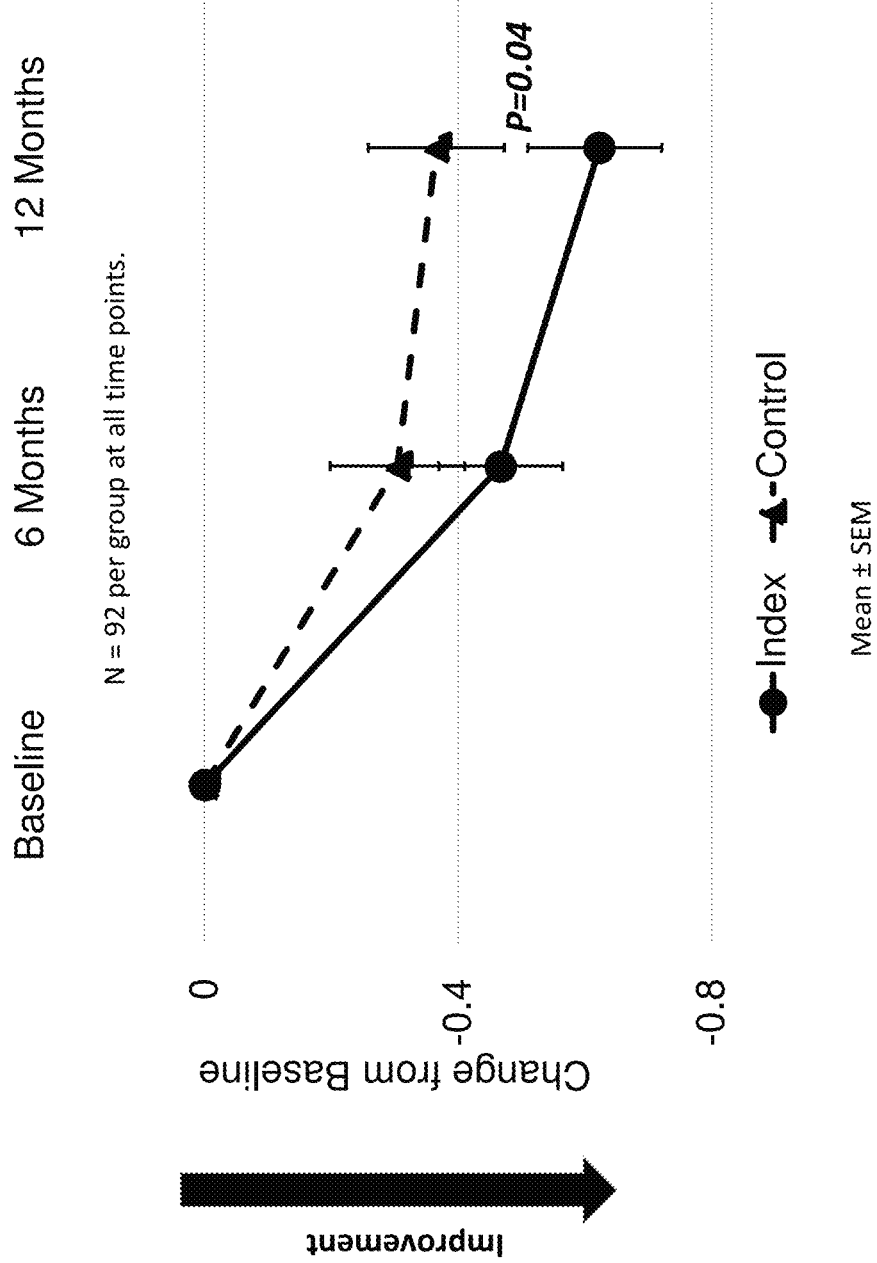

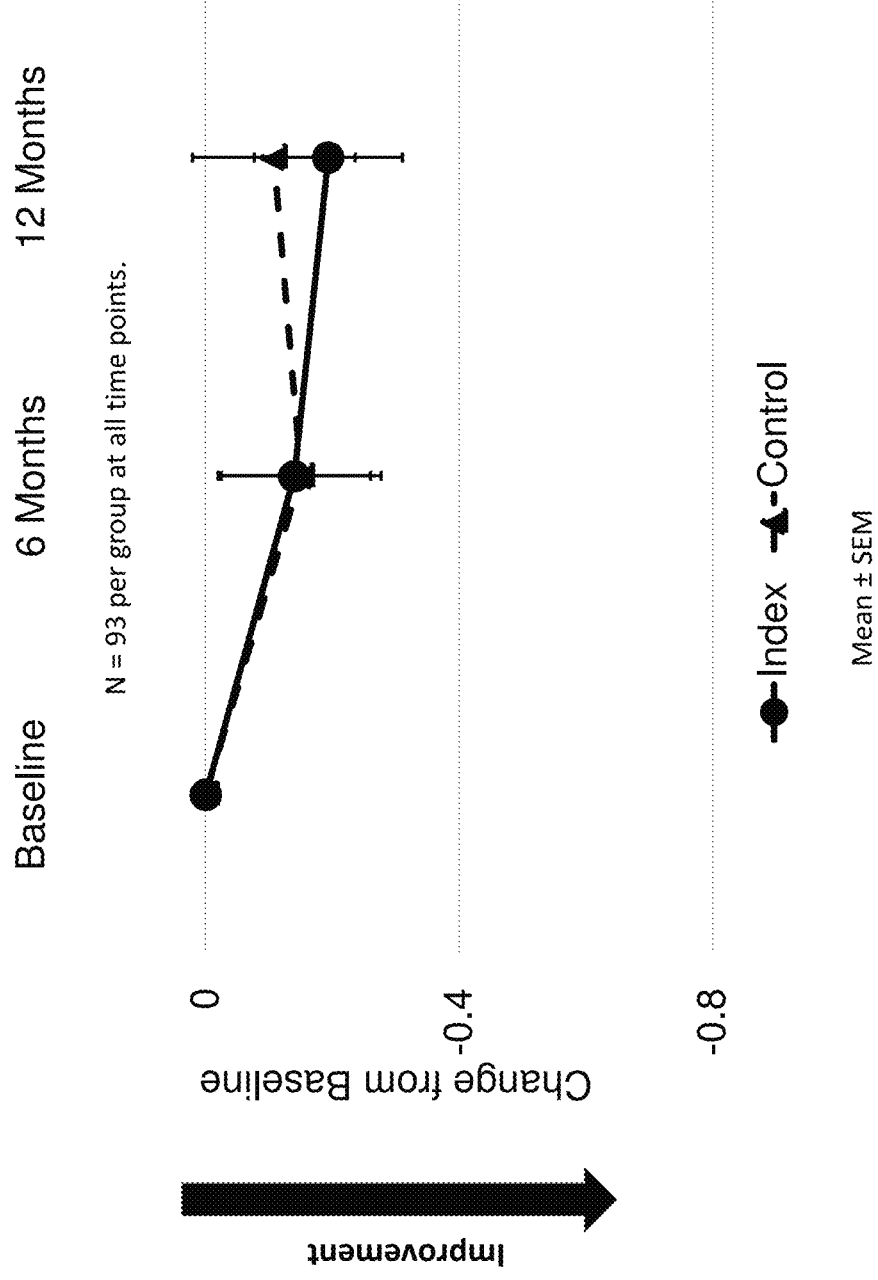

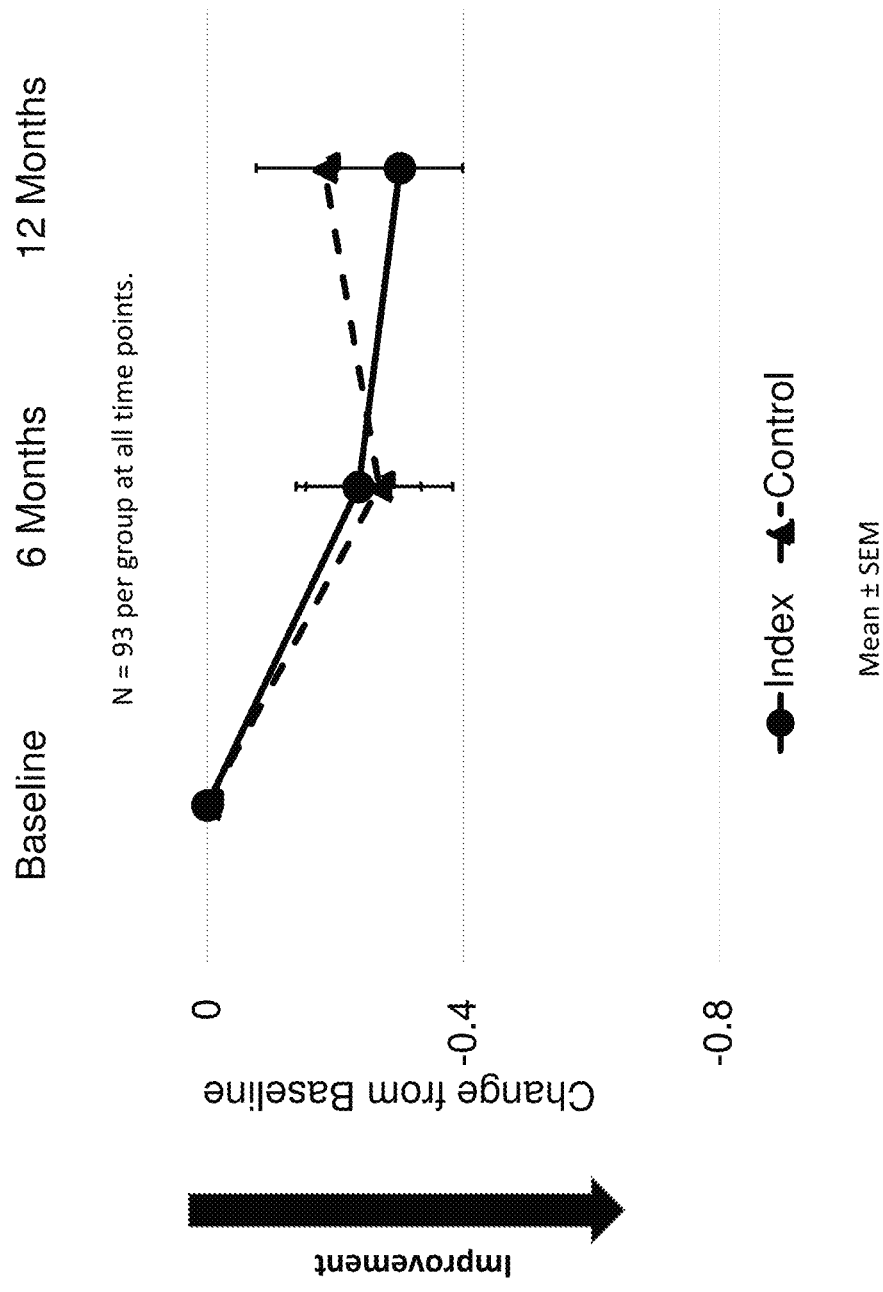
Figure 5: KOOS Pain Question 3
*Straightening knee fully moving*

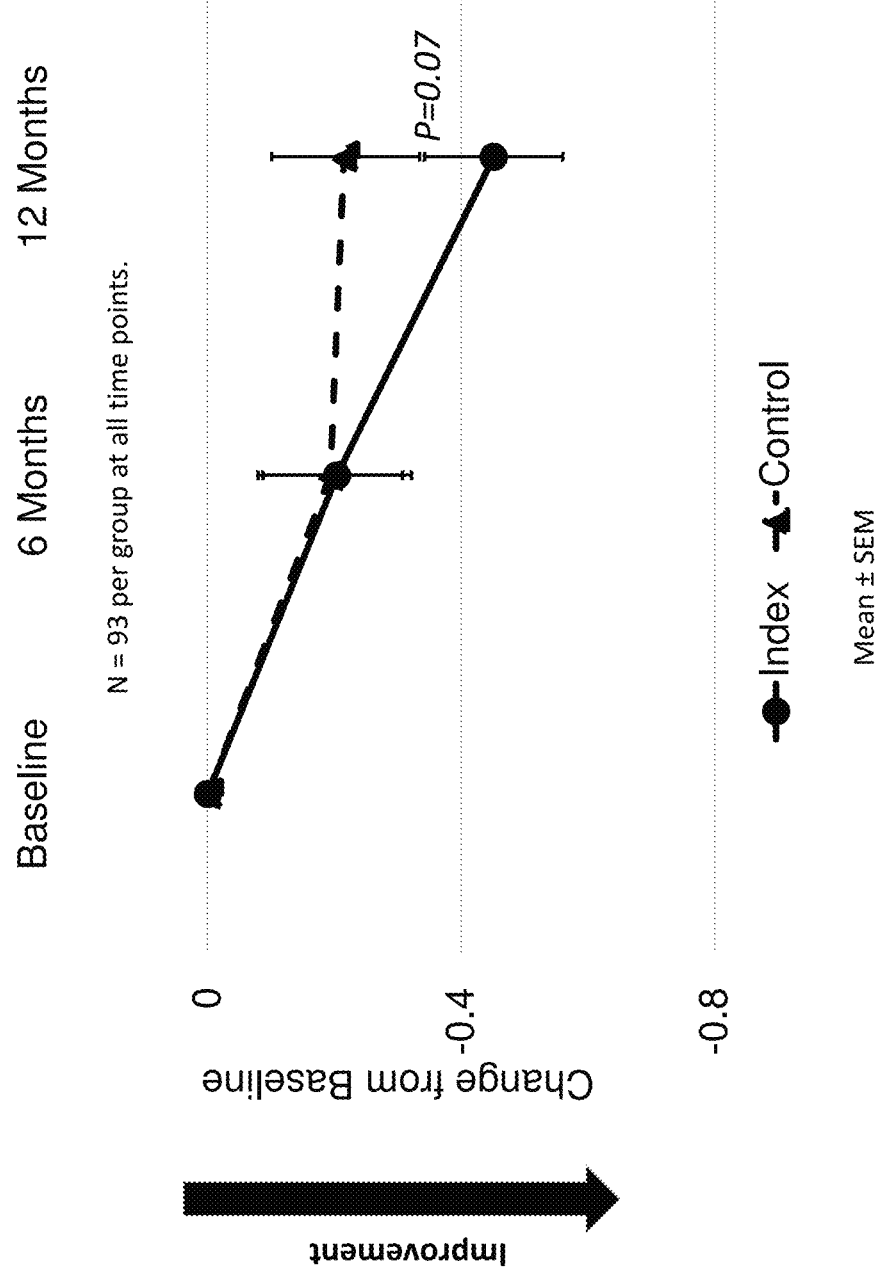
Figure 6: KOOS Pain Question 4
*Bending knee fully*

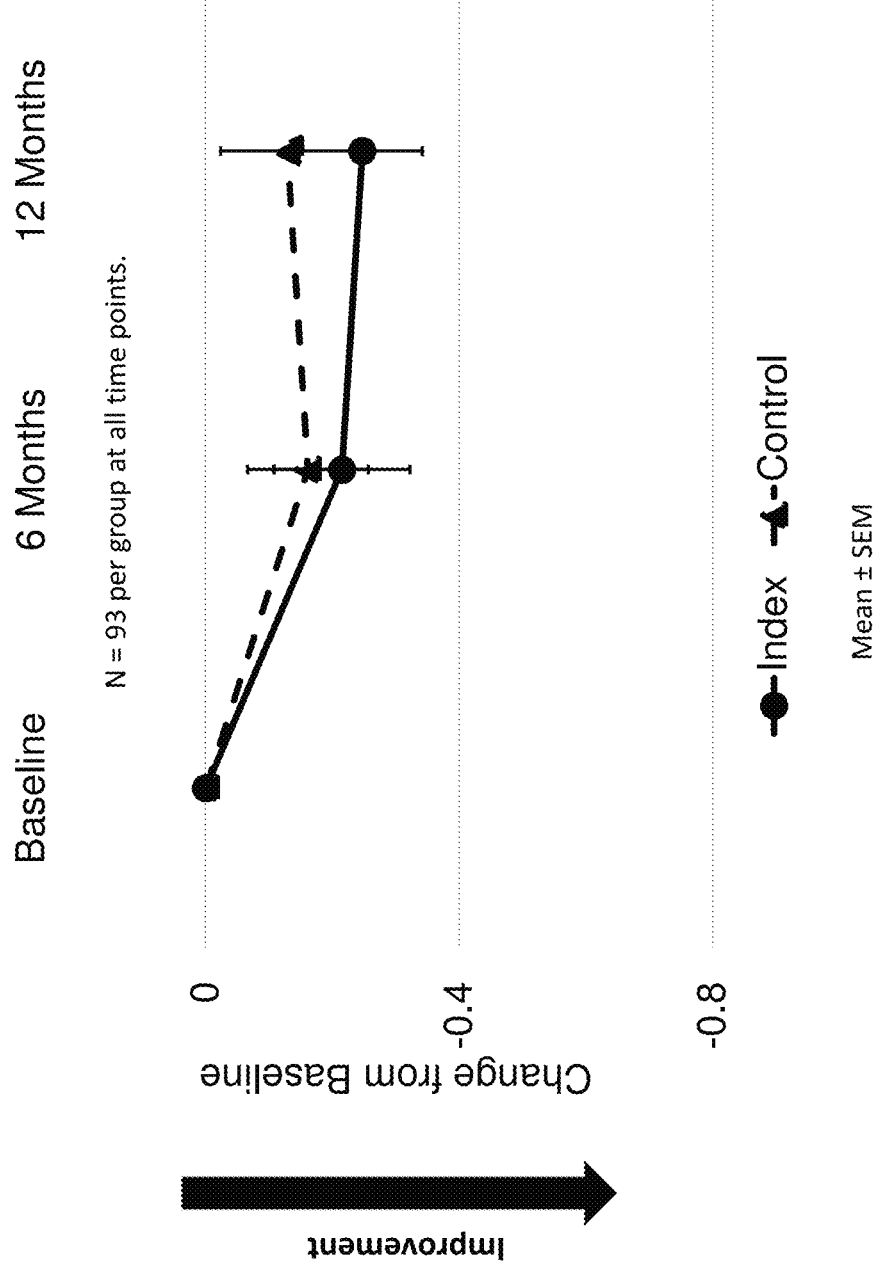

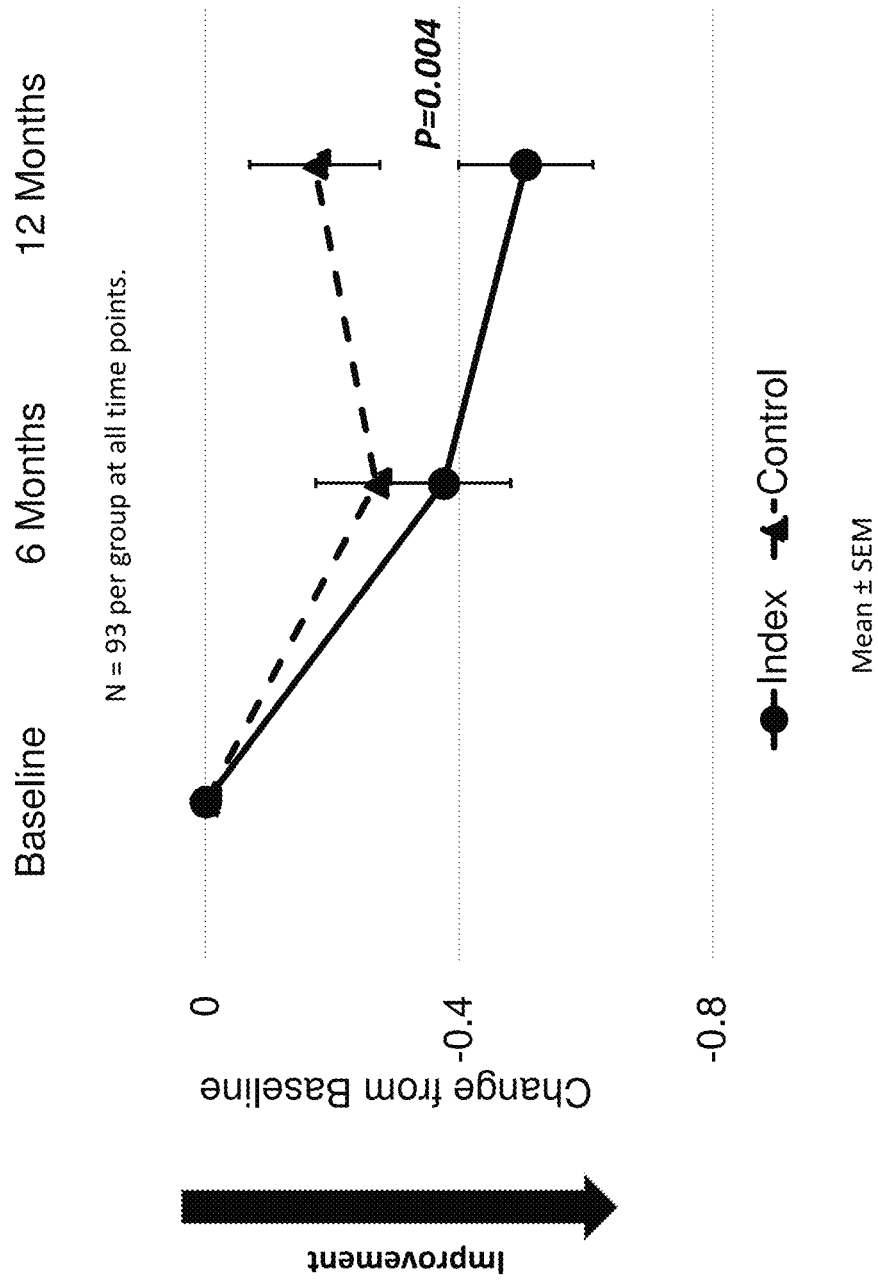

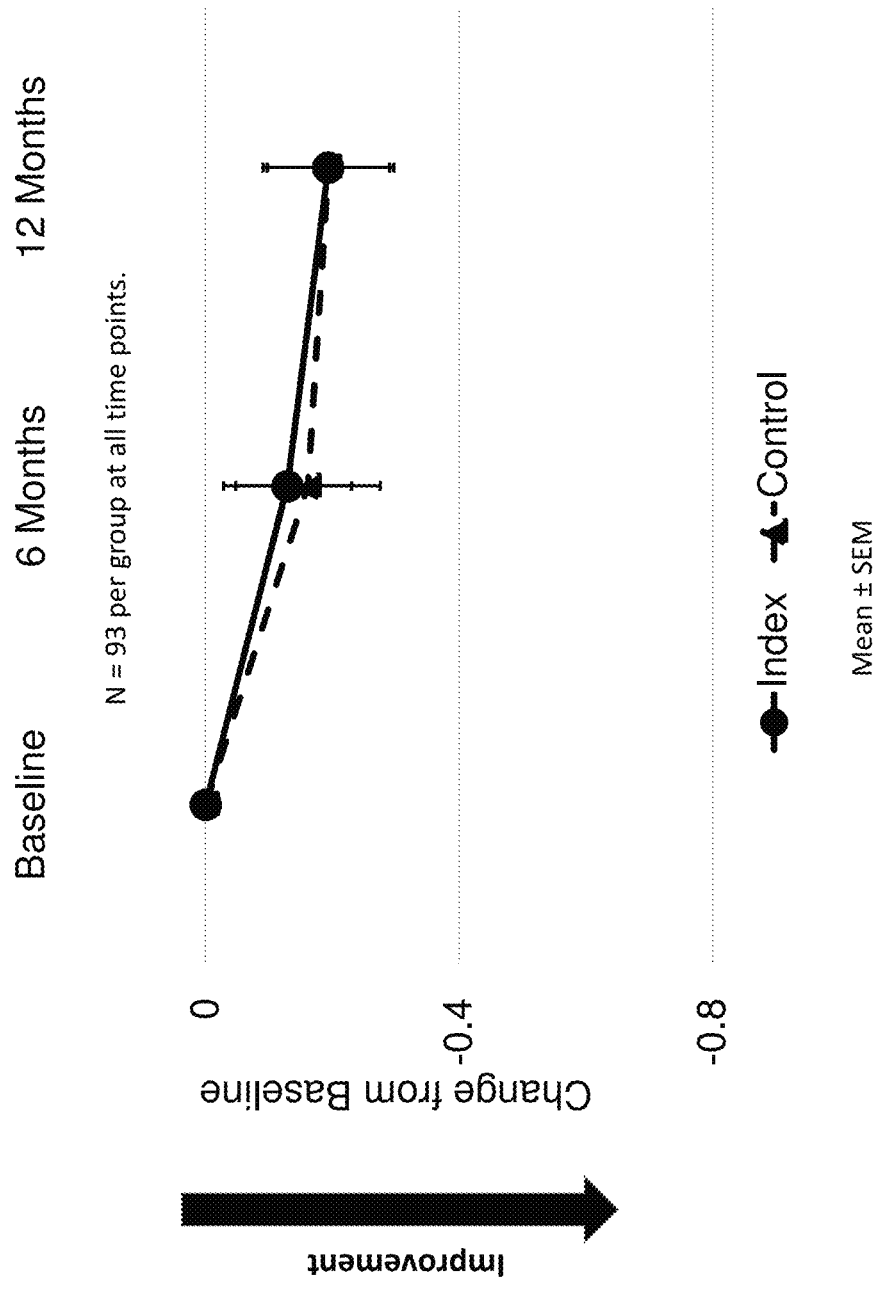
Figure 9: KOOS Pain Question 7
*At night while in bed*

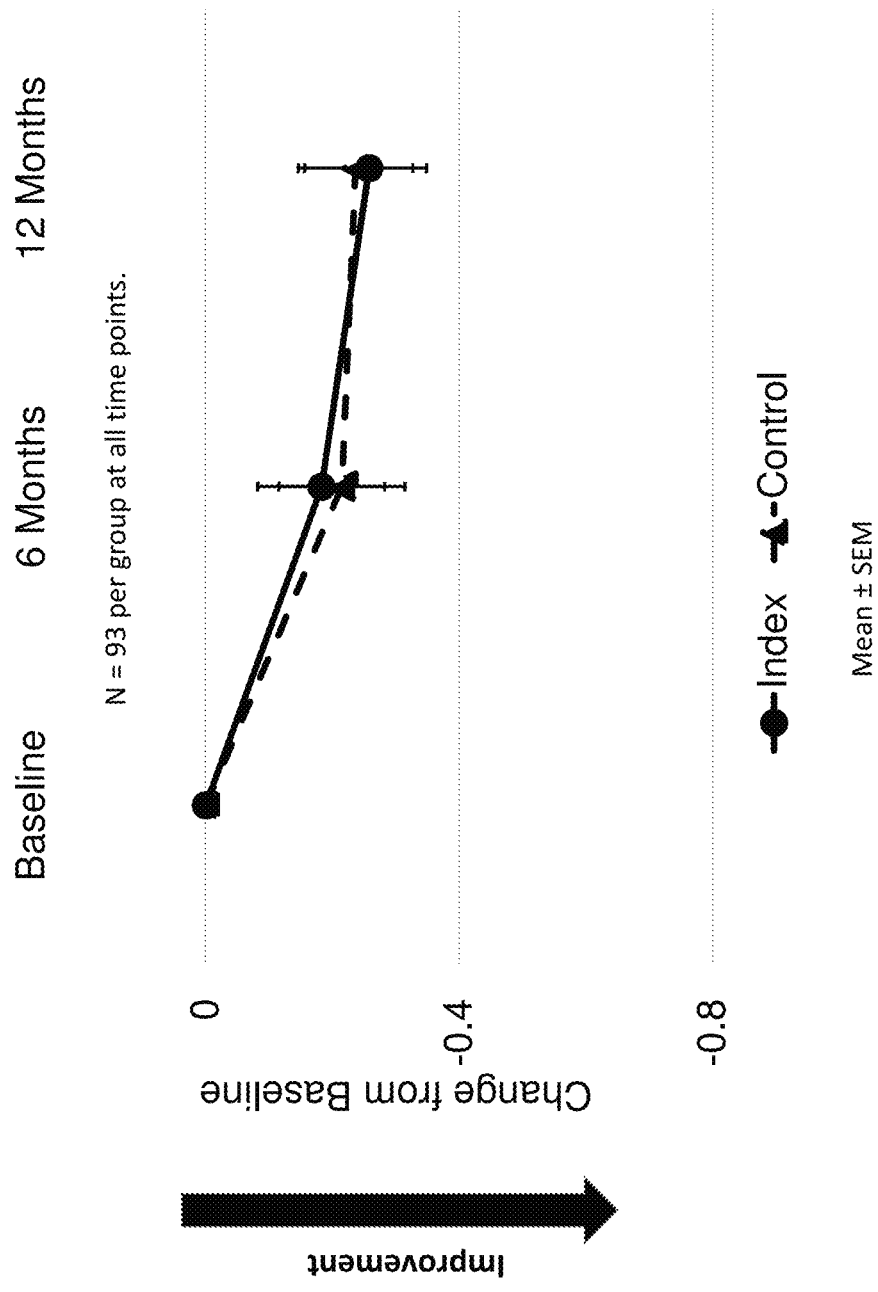
Figure 10: KOOS Pain Question 8
*Sitting or lying*

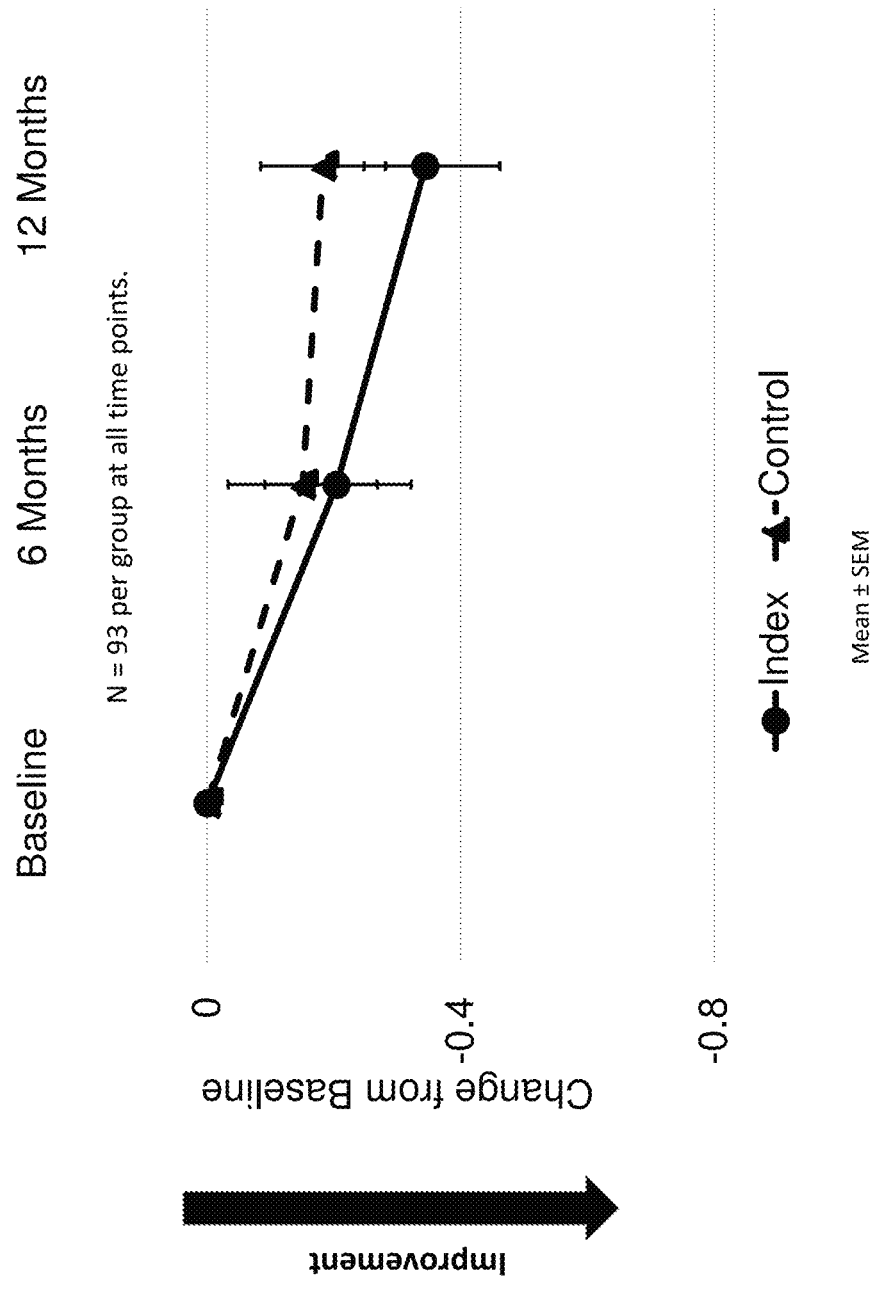

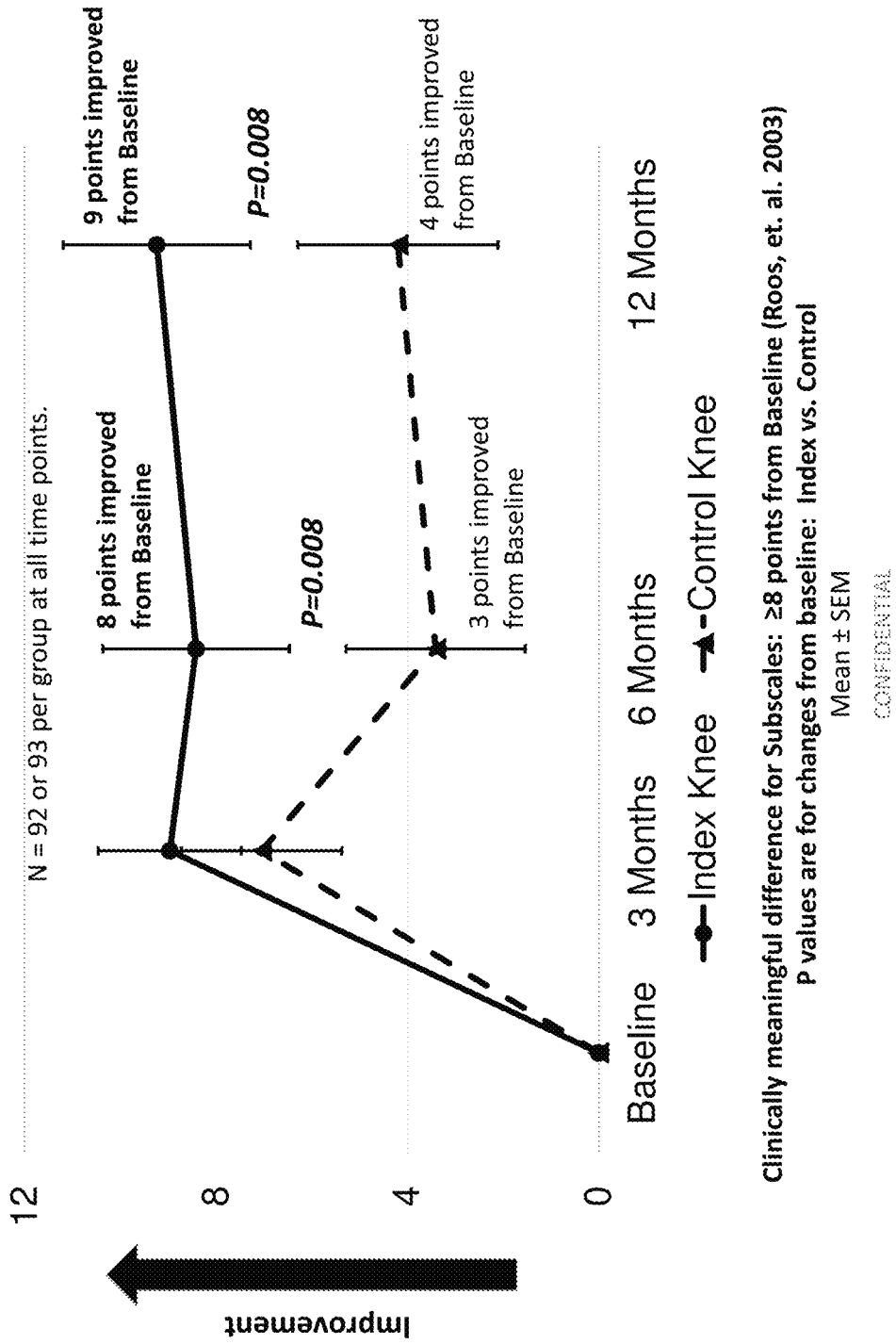
Figure 12: KOOS ADL – Changes from Baseline

METHOD OF MANAGING JOINT PAIN

FIELD OF THE INVENTION

The invention relates generally to methods for alleviating joint pain and specifically to alleviating joint pain in a patient during particular types of movement that exert pressure on the joint.

BACKGROUND

Joint pain is one of the major quality of life problems. Depending on which joint suffers from pain, it limits and sometimes totally disables movements or performance of specific works in daily living. If one suffers from pain in a joint in a leg such as hip, knee, and ankle, it limits leg movements and not only for hard activities such as running and jumping but routine ones such as walking and ascending or descending stairs. If one feels pain in one or more joints in her/his fingers, opening a cap of a container will become a challenging task.

While joint pain can be caused by a variety of reasons, including sometimes non-pathologic reasons, the most common cause is arthritis. According to the Center for Disease Control and Prevention March 2017 Vital Signs announced data estimating that 54.4 million U.S. adults suffer from arthritis, equating to about 25% of the population. The most common types of arthritis are osteoarthritis (OA), rheumatoid arthritis (RA), and gout. The data by the Center for Disease Control and Prevention also indicate that there are approximately 27 million OA and 1.3 million RA patients in the U.S. alone. Joint injury is another major cause of joint pain.

Osteoarthritis is the most common disease of the joints, and one of the most widespread of all chronic diseases. In the US, osteoarthritis (OA) is second only to heart disease as a cause of work disability in men over 50 years of age. Osteoarthritis was the 6th leading cause of years living with disability at a global level, accounting for 3% of the total global years of living with disability (Woolf 2003).

Approximately 80% of OA subjects need treatment in the knee. Within the knee joint of symptomatic individuals, the most common radiographic pattern for osteoarthritis is loss of articular (hyaline) cartilage and underlying subchondral bone, often with osteophyte formation at the joint margins. Both the tibio-femoral and patello-femoral compartments are commonly affected by degenerative changes. Patello-femoral arthritis due to loss of cartilage of the patella and trochlear groove is common in subjects with knee OA, whether or not other joint compartments have OA (Davies 2002, Lankhorst 2017).

Pain is a common subjective symptom in subjects with knee OA. Pain typically is treated with acetaminophen or non-steroidal anti-inflammatory drugs (NSAIDs). In addition, two types of intra-articular treatments, corticosteroids and hyaluronic acid products, also are used for pain control. Corticosteroid injections have been associated with further cartilage degeneration (McAlindon 2017), and are used less commonly than they used to be.

The hyaluronic acid products, or "viscosupplementation" products, are injected into the knee either in once-weekly divided doses (2 cc) for 3 weeks, or in a single larger dose (6 cc; Chevalier 2010). It is claimed for joint pain reduction for weeks to months (Cohen 1998), but multiple clinical trials failed to demonstrate their clinically meaningful efficacy. American Academy of Orthopaedic Surgeons/American Association of Orthopaedic Surgeons (AAOS) has issued, in its knee osteoarthritis treatment guideline published on May 18, 2013, a strong recommendation, which states, "We cannot recommend using hyaluronic acid for patients with symptomatic osteoarthritis of the knee." (http://www.aaos.org/cc_files/aaosorg/research/guidelines/treatmentofosteoarthritisofthekneeguideline.pdf) AAOS does not recommend use of corticosteroid injections, either, in the same guideline. Also, neither hyaluronic acid products nor corticosteroids are disease modifying.

Human articular (joint) cartilage is a unique tissue composed of chondrocytes embedded in an extracellular matrix of type II collagen, non-collagenous proteins, water, and specific proteoglycans. Proteoglycans contain various chondroitin and heparin sulfate groups which are able to be highly hydrated. This high degree of hydration is, to a large degree, what gives hyaline cartilage its resilience to compression and ability to buffer biomechanical stress. Articular cartilage is designed to enable smooth, almost frictionless movement of joint surface and to cushion long-term cyclic loads as well as off-set shear forces on the joint. The unique biomechanical properties of articular cartilage have never been matched by any artificial material, and are unmatched by fibrocartilage ("scar" cartilage) formed after microfracture surgery or other injuries. Unfortunately, articular cartilage does not regenerate naturally, neither after trauma nor in the setting of chronic "wear and tear" of aging (Buckwalter 2002).

Articular cartilage is a unique tissue in that it has no blood or nerve supply, and no inter-cellular connections. Typically, cartilage consists of water (c.a. 70%), extracellular matrix molecules such as Type II collagen and proteoglycan (c.a. 25%), and chondrocytes (c.a. 5%).

Thus far, only surgical methods and symptomatic (pain) management have been approved for subjects suffering with knee OA. Surgically, microfracture is used to induce formation of fibrocartilage (scar cartilage) by allowing bone marrow cells to infiltrate cartilage defects. However, fibrocartilage has much less structural strength and stability than normal articular cartilage and degenerates more quickly. Other invasive surgical procedures used for cartilage repair in the knee include drilling into subchondral bone and implanting plugs of cartilage cells (chondrocytes) or their progenitor cells that have been taken from non-weight-bearing parts of the subject's body or from a cadaver (osteochondral autograft/allograft transplantation, OATS procedure). Two surgeries are required, and the subject cannot return to full weight-bearing for approximately 6 weeks after the procedure. Treatment failures are common, as is the need for additional surgery for complications.

Two surgical procedures also are required for the autologous chondrocyte implantation (ACI), where healthy cartilage is harvested from the knee arthroscopically and grown in culture; then the cultured chondrocytes are implanted in open knee surgery where the cartilage is cut (debrided) down to the bone, either a periosteal for bioengineered flap is stitched or glued into place and the new cells are injected into the flap. In the published Carticel® study of more than 150 subjects with ACI, 49% of subjects required repeat surgery for various complications such as graft failure or delamination (Zaslav 2009). Complications include delamination, graft failure, and disturbed fusion (Niemeyer 2008).

The most invasive option thus far for subjects with disabling knee OA is joint replacement surgery, an expensive option with potential for serious morbid complications. Total knee replacement of one knee costs $35,000-70,000, which does not include the cost for a long (at least 6 weeks) rehabilitation process after the surgery and economical loss during the disabled period. This surgery is usually reserved for older subjects, since the prosthetic joint has a limited life expectancy and typically must be replaced after about 15 to 20 years.

Clearly a treatment that is safe, office-based, administered by familiar intra-articular injection methods, and that can promote regeneration of normal articular cartilage would address a critical unmet need. The regeneration of knee cartilage with normal morphological and biomechanical characteristics would not just delay or eliminate the need for invasive and expensive surgeries, including total knee replacement, but significantly improve the functions of the knees, thereby significantly reduce the disability associated with knee OA, as well as the loss in productivity that accompanies functional impairment.

Most joint health problems are due to either osteoarthritis (OA), rheumatoid arthritis (RA), or joint trauma. It is widely accepted that a common outcome of these conditions is cartilage damage. The patients with these conditions often suffer from limited joint mobility and function, presumably due to cartilage damage in the joint. If the damaged cartilage is repaired, the patient should be able to anticipate smoother movement of the joint.

A key issue associated with damaged joints is pain. According to an analysis of the Osteoarthritis Initiative (OAI) database, there is no correlation between the degree of cartilage damage and severity of joint pain experienced individuals (Bedson and Croft, BMC Musculoskeletal Disorders 2008, 9:116 doi: 10.1186/1471-2474-9-116). A person can have extreme joint pain with little or no observable cartilage damage in said joint. On the other hand, another person may feel little or no pain despite clear evidence of severe cartilage damage or destruction.

Articular cartilage does not have any neurons or vascularization. Although chondrocytes (cartilage cells) are embedded in the tissue, there are no inter-cellular connections as there are in bone for example. Therefore, cartilage repair should not directly influence joint pain. The only theoretical possibility where cartilage repair could alleviate pain is rebuilding a new cartilage tissue over exposed subchondral bone. However, as described above, no correlation has been found thus far between the cartilage damage or subchondral bone exposure versus severity of joint pain.

Joint pain is a major quality of life problem, with or without any apparent joint pathology such as OA, RA, or joint trauma. Although these conditions are commonly treated by anti-inflammatory agents or analgesics such as non-steroidal anti-inflammatory agent or acetaminophen, their efficacy is limited. In more extreme cases, some individuals use opioids to control the pain. However, opioid abuse has led to more stringent prescribing regulations, and opioids are not generally considered appropriate for long term pain management.

Peptide Injection

TPX-100 is a synthetic peptide consisting of 23 amino acids with amino acid sequence of TDLQERGDNDIS-PFSGDGQPFKD (SEQ ID No. 1), derived from human Matrix Extracellular Phosphoglycoprotein, or MEPE. TPX-100 has been shown to promote tissue-appropriate regeneration of cartilage, bone, and dentin without any soft tissue calcification or ossification. TPX-100 can be administered by conventional methods such as subcutaneous or intra-articular injection.

In non-clinical safety and efficacy studies, cartilage regeneration properties of TPX-100 have been demonstrated in the goat model of standardized large cartilage defects. In a full-thickness chondral defect model in weight-bearing goats, a regimen of four weekly intra-articular (IA) injections of TPX-100 (125 mg and 250 mg) was associated with histologically-confirmed and statistically significant articular cartilage regeneration at 6 months post-surgery compared to cartilage regeneration in the vehicle control group. The drug was safe and well-tolerated in these freely ambulatory animals (See U.S. Pat. No. 8,426,558). Safety of the TPX-100 peptide was further confirmed in multiple GLP toxicology studies, as well as multiple Phase 1 and Phase 2 clinical studies involving systemic and local injections of the drug.

Based on these safety and articular cartilage regeneration efficacy data, a randomized, double-blind, placebo-controlled clinical study of TPX-100 with the subjects with osteoarthritis of the knees was performed. Successful clinical development of TPX-100 could result in its selection as the first-line treatment for OA, prior to surgical options. TPX-100 has the potential to reduce significantly the disability associated with knee OA as well as the loss in productivity that accompanies functional impairment. Significant improvement in knee functions was particularly anticipated as the primary knee health effect by adequate repair of knee cartilage.

The TPX-100 drug substance was manufactured as the acetate salt lyophilized powder with the C-terminus amidated. The TPX-100 injection (drug product) used in the clinical study was formulated in a saline solution of pH7.

The TPX-100 drug substance is also manufactured as the sodium salt lyophilized powder utilizing the amidated C-terminus. This sodium salt is being used in the latest lyophilized formulation of TPX-100, which is reconstituted with water for injection (WFI) before its therapeutic use in humans or other species.

SUMMARY OF THE INVENTION

A method of alleviating joint pain associated with activities that exert stress or pressure on the joint is disclosed. The method comprises injecting the patient with a formulation of a peptide of SEQ ID No. 1 in a therapeutically effective amount.

In an important aspect of the invention, method of alleviating knee pain associated with activities that exert a high degree of stress or pressure on the knee such as climbing stairs is disclosed. The method comprises injecting the patient with a formulation of a peptide of SEQ ID No. 1 in a therapeutically effective amount.

An aspect of the invention is alleviating knee pain in a patient wherein the pain alleviation is focused on situations where the patient is exerting pressure on the knee and bending the knee in a manner alleviating knee pain in a patient while the patient needs to exert more pressure on the knee such as going up or down stairs. The method includes diagnosing the patient that is experiencing knee pain during such movement, and then administering to the patient a formulation comprised of a therapeutically effective amount of a peptide of SEQ ID. No. 1.

The peptide is formulated into an injectable formulation, which can include water or saline solution and be injected locally into the joint such as a knee joint subcutaneously or intra-articular.

In an aspect of the invention, the method is carried out with the injection being administered only once, only twice, three times, four times, five times, etc. The dosing may be delivered daily, every three days, once a week, every ten days, every other week, once a month, every other month, every three months, every six months, once a year, or different combinations thereof. Injection can be local or systemic. It can be intra-articular, subcutaneous, intramuscular, or intravenous. Injection is not an only way for administration. The peptide of SEQ ID. No. 1 can be administered with a biodegradable matrix carrier such as collagen sponge, hyaluronic acid, alginate, and so forth, and such combination can be implanted into a cartilage defect or injected into the knee or any other joint with pain.

In an aspect of the invention, the method is used to treat any joint pain regardless of its bottom-line pathology. It can be used to treat joint pain caused by osteoarthritis (OA), rheumatoid arthritis (RA), gout, joint injury, or any other causes insofar as they result in joint pain.

In an aspect of the invention, the method includes follow up evaluation of the patient's knee pain using systems such as the pain subscale of knee injury and osteoarthritis outcome score (KOOS). The evaluation may also be carried out based on any other patient reported outcome (PRO) assessing the severity of knee pain, including but not limited to the pain subscale of Western Ontario and McMaster Universities Osteoarthritis Index (WOMAC) and numerical rating scale of pain (NRS). If the patient's pain is not in the knee but other joint, a pain evaluation system applicable to the joint may be used. Broadly used pain evaluation systems are visual analogue scale (VAS), visual rating scale (VRS), and NRS. Also, there are other joint-specific pain scales. For example, if the target joint to treat the pain is hip, hip disability and osteoarthritis outcome score (HOOS) may be used.

In an aspect of the invention, the dosing may be in a range of from 20 mg to 1,200 mg, or 25 mg to 600 mg, 100 mg to 400 mg, or 200 mg, wherein all milligram doses are ±20%, ±10%, ±5%.

In an aspect of the invention, the patient with knee pain is first evaluated based on whether or not they feel knee pain, particularly when they bend their knees.

An aspect of the invention is a method for managing joint pain in a subject, comprising:
combining water with a peptide consisting only of an amino acid sequence TDLQERGDNDISPFSGDGQPFKD (SEQ. ID No: 1); and
injecting a joint of the subject with the injectable aqueous formulation,
whereby the formulation reduces joint pain in the subject absent observable damage in cartilage of the joint.

An aspect of the invention is a method for managing joint pain in a subject, comprising:
combining water with a lyophilized powder of a peptide consisting only of an amino acid sequence TDLQERGDNDISPFSGDGQPFKD (SEQ. ID No: 1); and
injecting a joint of the subject with the injectable aqueous formulation,
whereby the formulation reduces joint pain in the subject absent detectable damage in cartilage of the joint.

An aspect of the invention is a method for managing knee joint pain in a subject, comprising:
combining water with a powder of a peptide consisting only of an amino acid sequence TDLQERGDNDISPFSGDGQPFKD (SEQ. ID No: 1); and
injecting a joint of the subject with the injectable aqueous formulation,
whereby the formulation reduces joint pain in the subject.

An aspect of the invention is a method for managing joint pain in a subject, comprising:
combining water with lyophilized powder of a peptide consisting only of an amino acid sequence TDLQERGDNDISPFSGDGQPFKD (SEQ. ID No: 1) the sequence comprising an amidated C-terminus to create an injectable aqueous formulation; and
injecting a joint of the subject with the injectable aqueous formulation,
whereby the formulation reduces joint pain in the subject.

An aspect of the invention is a method for managing knee joint pain in a subject, comprising:
combining water with a peptide consisting only of an amino acid sequence TDLQERGDNDISPFSGDGQPFKD (SEQ. ID No: 1) the sequence comprising an amidated C-terminus to create an injectable aqueous formulation; and
injecting a joint of the subject with the injectable aqueous formulation,
whereby the formulation reduces joint pain in the subject.

An aspect of the invention is a method for managing joint pain in a subject, comprising:
combining water with a peptide consisting of an amino acid sequence TDLQERGDNDISPFSGDGQPFKD (SEQ. ID No: 1) the sequence comprising an amidated C-terminus to create an injectable aqueous formulation; and
injecting a joint of the subject with the injectable aqueous formulation,
whereby the formulation reduces joint pain in the subject.

An aspect of the invention is a method for managing joint pain in a subject, comprising:
combining water with a peptide consisting of an amino acid sequence TDLQERGDNDISPFSGDGQPFKD (SEQ. ID No: 1) to create an injectable aqueous formulation; and
injecting a joint of the subject with the injectable aqueous formulation,
whereby the formulation reduces joint pain in the subject.

An aspect of the invention is a method for managing knee joint pain in a subject, comprising:
combining water with a sodium salt lyophilized powder of a peptide consisting only of an amino acid sequence TDLQERGDNDISPFSGDGQPFKD (SEQ. ID No: 1) the sequence comprising an amidated C-terminus to create an injectable aqueous formulation; and
injecting a knee joint of the subject with the injectable aqueous formulation,
whereby the formulation reduces joint pain in the subject.

An aspect of the invention is a method for managing knee joint pain in a subject, comprising:
combining water with a lyophilized powder of a peptide consisting only of an amino acid sequence TDLQERGDNDISPFSGDGQPFKD (SEQ. ID No: 1) the sequence comprising an amidated C-terminus to create an injectable aqueous formulation; and
injecting a knee joint of the subject with the injectable aqueous formulation,
whereby the formulation reduces joint pain in the subject.

An aspect of the invention is a method for managing knee joint pain in a subject, comprising:
combining water with a peptide consisting only of an amino acid sequence TDLQERGDNDISPFSGDGQPFKD (SEQ. ID No: 1) the sequence comprising an amidated C-terminus to create an injectable aqueous formulation; and
injecting a knee joint of the subject with the injectable aqueous formulation,
whereby the formulation reduces joint pain in the subject.

An aspect of the invention is a method for managing knee joint pain in a subject, comprising:
combining water with a peptide consisting of an amino acid sequence TDLQERGDNDISPFSGDGQPFKD (SEQ. ID No: 1) the sequence comprising an amidated C-terminus to create an injectable aqueous formulation; and injecting a knee joint of the subject with the injectable aqueous formulation, whereby the formulation reduces joint pain in the subject.

An aspect of the invention is a method for managing knee joint pain in a subject, comprising:

combining water with a peptide consisting of an amino acid sequence TDLQERGDNDISPFSGDGQPFKD (SEQ. ID No: 1) to create an injectable aqueous formulation; and injecting a knee joint of the subject with the injectable aqueous formulation, whereby the formulation reduces joint pain in the subject.

An aspect of the invention is a method for managing knee joint pain in a subject, comprising:

combining water with a sodium salt lyophilized powder of a peptide consisting only of an amino acid sequence TDLQERGDNDISPFSGDGQPFKD (SEQ. ID No: 1) the sequence comprising an amidated C-terminus to create an injectable aqueous formulation; and injecting a knee joint of the subject with the injectable aqueous formulation, whereby the formulation reduces joint pain in the subject absent any observable change in cartilage of the knee joint after the injection.

An aspect of the invention is a method for managing knee joint pain in a subject, comprising:

combining water with a sodium salt lyophilized powder of a peptide consisting only of an amino acid sequence TDLQERGDNDISPFSGDGQPFKD (SEQ. ID No: 1) the sequence comprising an amidated C-terminus to create an injectable aqueous formulation; and injecting a knee joint of the subject with the injectable aqueous formulation, whereby the formulation reduces joint pain in the subject.

An aspect of the invention is a method for managing knee joint pain in a subject, comprising:

combining water with a lyophilized powder of a peptide consisting only of an amino acid sequence TDLQERGDNDISPFSGDGQPFKD (SEQ. ID No: 1) the sequence comprising an amidated C-terminus to create an injectable aqueous formulation; and injecting a knee joint of the subject with the injectable aqueous formulation, whereby the formulation reduces joint pain in the subject.

An aspect of the invention is a method for managing knee joint pain in a subject, comprising:

combining water with a peptide consisting only of an amino acid sequence TDLQERGDNDISPFSGDGQPFKD (SEQ. ID No: 1) the sequence comprising an amidated C-terminus to create an injectable aqueous formulation; and injecting a knee joint of the subject with the injectable aqueous formulation, whereby the formulation reduces joint pain in the subject.

An aspect of the invention is a method for managing knee joint pain in a subject, comprising:

combining water with a peptide consisting of an amino acid sequence TDLQERGDNDISPFSGDGQPFKD (SEQ. ID No: 1) the sequence comprising an amidated C-terminus to create an injectable aqueous formulation; and injecting a knee joint of the subject with the injectable aqueous formulation, whereby the formulation reduces joint pain in the subject.

An aspect of the invention is a method for managing knee joint pain in a subject, comprising:

combining water with a peptide consisting of an amino acid sequence TDLQERGDNDISPFSGDGQPFKD (SEQ. ID No: 1) the sequence comprising an amidated C-terminus to create an injectable aqueous formulation; and injecting a knee joint of the subject with the injectable aqueous formulation, whereby the formulation reduces joint pain in the subject.

An aspect of the invention is a method for managing knee joint pain in a subject, comprising:

combining water with a peptide consisting of an amino acid sequence TDLQERGDNDISPFSGDGQPFKD (SEQ. ID No: 1) to create an injectable aqueous formulation; and injecting a knee joint of the subject with the injectable aqueous formulation, whereby the formulation reduces joint pain in the subject.

An aspect of the invention includes a method of treatment or a use for a composition as described herein wherein the peptide of SEQ ID No: 1 is administered (intra-articular injection) in an aqueous formulation comprising water for injection (WFI) in an amount in a range of 100 mg to 400 mg wherein the injection is intra-articular, wherein the formulation is created by mixing the WFI with a lyophilized powder of the peptide of SEQ ID NO: 1 just prior to injection, and further wherein the formulation may be injected in an amount of 200 mg per injection every five days, week, 10 days, 15 days pro re nata (PRN) for a period of two, three, four or five injections or more after which the results are evaluated on a pain subscale of either or both of WOMAC or KOOS and/or using a numerical rating scale for pain (NRS).

An aspect of the invention is a method as described above, further comprising:

diagnosing the patient as experiencing joint pain when the patient is undergoing an activity which requires a stress to the joint.

An aspect of the invention is a method as described above, where the activity which requires a stress is a greater degree of knee bending than necessary to walk on a flat surface.

An aspect of the invention is a method as described above, where the activity is going up or down stairs.

An aspect of the invention is a method as described above, where the patient suffers from at least one of the following conditions in the painful joint: osteoarthritis, rheumatoid arthritis, or joint trauma.

An aspect of the invention is a method as described above, whereby the patient is diagnosed as experiencing less pain going up or down stairs after the injecting.

An aspect of the invention is a method for reducing the frequency of overall joint pain experienced by a subject, comprising:

injecting a joint of the subject with the injectable aqueous formulation comprising an amino acid sequence TDLQERGDNDISPFSGDGQPFKD (SEQ. ID No: 1), evaluating joint pain in the subject 12 months or earlier after administering the formulation, whereby the formulation reduces joint pain in the subject absent any observable change in cartilage of the joint.

While it may take months to reduce the frequency of joint pain after the initial treatment of the joint with the formulation, the pain should be consistently controlled when the treatment is continued with reasonable intervals such as once every 6 months or once a year—pro re nata (PRN).

An aspect of the invention is a method for reducing the frequency of overall joint pain experienced by a subject, comprising:

injecting a joint of the subject with the injectable aqueous formulation comprising an amino acid sequence TDLQERGDNDISPFSGDGQPFKD (SEQ. ID No: 1), evaluating joint pain in the subject after administering the formulation, whereby the formulation reduces joint pain in the subject.

An aspect of the invention is a method as described above where the joint is knee.

An aspect of the invention is a method as described above wherein the injection is intra-articular.

An aspect of the invention is a method as described above wherein the peptide of SEQ ID NO: 1 is administered in combination with hyaluronic acid.

An aspect of the invention is a method as described above wherein the peptide is administered in a dose in a range of 20 mg to 1,200 mg per one injection.

An aspect of the invention is a method for managing joint pain in a subject, comprising:

injecting a joint of the subject with an injectable aqueous formulation comprising a peptide consisting only of an amino acid sequence TDLQERGDNDISPFSGDGQPFKD (SEQ. ID No: 1), whereby the formulation reduces joint pain in the subject.

An aspect of the invention is a method for managing joint pain in a subject, comprising:

making a first evaluation of knee pain of the patient using a pain subscale of Western Ontario and McMaster Universities Osteoarthritis Index (WOMAC);

injecting a knee joint of the subject with an injectable aqueous formulation comprising a peptide consisting only of an amino acid sequence TDLQERGDNDIS-PFSGDGQPFKD (SEQ. ID No: 1), making a second evaluation of knee pain of the patient using a WOMAC;

whereby the formulation reduces joint pain in the subject based on WOMAC.

An aspect of the invention is a method for managing joint pain in a subject, comprising:

making a first evaluation of the patient's knee pain using a pain subscale of knee injury and osteoarthritis outcome score (KOOS);

injecting a knee joint of the subject with an injectable aqueous formulation comprising a peptide consisting only of an amino acid sequence TDLQERGDNDIS-PFSGDGQPFKD (SEQ. ID No: 1), making a second evaluation knee pain of the patient using a KOOS;

whereby the formulation reduces knee joint pain in the subject based on KOOS.

An aspect of the invention is a method for managing joint pain in a subject, comprising:

making a first evaluation of the patient's joint pain using a suitable patient reported outcome to said joint;

injecting a joint of the subject with an injectable aqueous formulation comprising a peptide consisting of an amino acid sequence TDLQERGDNDISPFSGDGQPFKD (SEQ. ID No: 1), making a second evaluation knee pain of the patient using the same patient reported outcome;

whereby the formulation reduces knee joint pain in the subject based on the same patient reported outcome.

Examples of the patient reported outcome usable to evaluate patient's joint pain other than WOMAC and KOOS include Numerical Rating Scale, Visual Analogue Scale, Visual Rating Scale, Brief Pain Inventory, Descriptor Differential Scale, Lequesne-Algofunctional Index, Mankoski Pain Scale, McGill Pain questionnaire, Oswestry Disability Index, and Verbal Rating Scale.

An aspect of the invention is a method for managing hip joint pain in a subject, comprising:

making a first evaluation of the patient's hip joint pain using the pain subscale of Hip Osteoarthritis Outcome Scale (HOOS);

injecting the hip joint of the subject with an injectable aqueous formulation comprising a peptide consisting of an amino acid sequence TDLQERGDNDISPFSGDGQPFKD (SEQ. ID No: 1), making a second evaluation of hip pain of the patient using HOOS;

whereby the formulation reduces hip joint pain in the subject based on HOOS.

The invention includes uses, including:

A use of a formulation comprising a therapeutically effective amount of a peptide of SEQ. ID No. 1 alleviating knee pain in a patient diagnosed knee pain when the patient is undergoing an activity which requires a greater degree of knee bending than walking A use of a peptide in the manufacture of a formulation for alleviating knee pain in a patient, wherein the patient is diagnosed with knee pain when the patient is undergoing an activity which requires a greater degree of knee bending than walking; and wherein the peptide consists of sequence TDLQERGDNDISPFSGDGQPFKD (SEQ. ID No: 1).

The use as indicted herein where the formulation reduces knee pain in the subject without improving cartilage structure.

The use as indicted above where the subject is diagnosed with articular cartilage damage.

The use as indicted herein where the formulation reduces knee pain in the patient in the absence of an observable effect on cartilage structure.

The use as indicted herein where the administering is by injection.

The use as indicted herein where the injection is a local injection to a knee of the patient.

The use as indicted herein where wherein the injection is intra-articular

The use as indicted herein where the injection is subcutaneous.

The use as indicted herein where wherein the peptide of SEQ ID NO:1 is administered with a biodegradable matrix carrier.

The use as indicted herein where the biodegradable carrier is a biodegradable collagen sponge.

The use as indicted herein where the peptide of SEQ ID NO: 1 is administered in combination with hyaluronic acid.

The use as indicted herein where the peptide of SEQ ID NO: 1 is administered in combination with alginate.

The use as indicted herein where evaluating knee pain in the patient takes place one month or more after the administering, wherein the evaluating is while the patient is undergoing the motion.

The use as indicted herein where the evaluating is based on a knee injury and osteoarthritis outcome score (KOOS).

The use as indicted herein where the evaluating is based on one or more of patients reported outcomes (PROs) assessing knee pain.

The use as indicted herein where the motion is ascending or descending stairs.

The use as indicted herein where the administering is repeated pro re nata (PRN).

The use as indicted herein where the administering is repeated two or more times every three days or more for a period of 300 days.

The use as indicted herein where the administering is repeated once each week for four times to both of the patient's knees.

The use as indicted herein where the peptide is administered in a dose in a range of 20 mg to 1,200 mg per one injection.

The use as indicted herein where the patient was diagnosed with patello-femoral osteoarthritis in both knees.

The use as indicted herein where the patient meets all inclusion criteria herein and does not have any exclusion criteria listed herein.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1 is a graph showing the results of an actual clinical study showing changes of knee pain from base line over 12 months based on the pain subscale of knee injury and osteoarthritis outcome score (KOOS).

FIG. 2 is an outline of questions asked to patients in connection with the study described herein.

FIG. 3 is a graph showing the results obtained in answer to question 1 relating to how often knee pain is experienced in each knee.

FIG. 4 is a graph showing the results obtained in answer to question 2 relating to the severity of knee pain experienced when twisting/pivoting on each knee in the preceding week.

FIG. 5 is a graph showing the results obtained in answer to question 3 relating to the severity of knee pain experienced when straightening each knee fully in the preceding week.

FIG. 6 is a graph showing the results obtained in answer to question 4 relating to the severity of knee pain experienced when bending each knee fully in the preceding week.

FIG. 7 is a graph showing the results obtained in answer to question 5 relating to the severity of knee pain experienced in each knee when walking on a flat surface in the preceding week.

FIG. 8 is a graph showing the results obtained in answer to question 6 relating to the severity of knee pain experienced in each knee when going up or down stairs in the preceding week.

FIG. 9 is a graph showing the results obtained in answer to question 7 relating to the severity of knee pain experienced in each knee while in bed in the preceding week.

FIG. 10 is a graph showing the results obtained in answer to question 8 relating to the severity of knee pain experienced in each knee when sitting or lying in the preceding week.

FIG. 11 is a graph showing the results obtained in answer to question 9 relating to the severity of knee pain experienced in each knee while standing up right in the preceding week.

FIG. 12 is a graph showing the results of actual clinical study showing changes of knee function from base line over 12 months measured by KOOS ADL (function of daily living subscale of knee injury and osteoarthritis outcome score).

DETAILED DESCRIPTION OF THE INVENTION

Before the present methods, uses and formulations are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an injection" includes a plurality of such injections and reference to "the measurement" includes reference to one or more measurements and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Joint Pain and its Treatment

Pain associated with arthritis or injuries tends to be felt more severely when the joint is under more physical stress. This is common among joint disorders such as osteoarthritis, rheumatoid arthritis, and joint trauma.

Anti-inflammatory agents such as non-steroidal anti-inflammatory drugs (NSAIDs) and analgesic such as acetaminophen are currently used to control joint pain. These drugs tend to work better when the pain is milder. In more severe cases, these types of agents tend to be less effective. As such, opioids are sometimes used to control severe joint pain but opioid use is not desirable or ideal for these patients. Also, in case of NSAIDs, their uses need to be carefully monitored because they are known to be associated with multiple adverse effects such as kidney malfunction and stomach bleeding. Use of these drugs are often avoided by physicians particularly in elderly patients since they may already have deteriorated kidney functions.

In the present invention, a method of alleviating joint pain that works better on pain associated with activities involving a higher degree of stress on the joint is disclosed. The method comprises injecting the patient with a formulation of a peptide of SEQ ID No. 1 in a therapeutically effective amount. This method particularly works well in alleviating knee pain associated with stress on the knee, without safety concerns such as those with opioid analgesic.

The peptide of SEQ ID No. 1 has been known to promote new cartilage formation (See U.S. Pat. No. 8,426,558).

For this activity, the peptide of SEQ ID No. 1 was tested for its clinical safety and efficacy on a condition involving cartilage damage in a Phase 2 randomized double-blind controlled clinical trial with mild to severe knee osteoarthritis (OA) patients. See EXAMPLES.

For its selective cartilage repair activities, the expected clinical benefit of the peptide was improvement of knee functions because better movement of a joint could be anticipated if the peptide repairs the damaged cartilage, makes it resilient and its surface smoother.

On the other hand, pain alleviation was not anticipated since it has been known that the peptide of SEQ ID No. 1 does not have any anti-inflammatory or analgesic activities.

Also, cartilage repair should not affect any sensations since cartilage does not have neurons and there is no inter-cellular connection among chondrocytes (cartilage cells) embedded in the cartilage tissue.

As expected, knee functions measured by KOOS (Knee injury and Osteoarthritis Outcome Score) and WOMAC (Western Ontario and McMaster Universities Osteoarthritis Index) demonstrated clinically meaningful and highly statistically significant (p=0.008) improvement in the knees treated with the peptide of SEQ ID No. 1 as compared to the placebo-treated knees at both 6 and 12-month time points after treatment. See FIG. 12.

The KOOS ADL (Function of Daily Living) consists of 17 questions asking degree of difficulty in functioning each knee during 17 different activities in daily living. Those 17 activities are broadly ranged from light to heavy duties. With regard to each activity, difficulty of each knee function is scored in 0-4 range where 0 as no difficulty and 4 as the most difficulty. The sum of the scores range from 0 to 68 (4×17), which is then converted to a 0-100 scale is KOOS ADL score. WOMAC function consists of the same questions with same scoring, except the total score range is not converted to 0-100 but remains 0-68.

The function improvement in the knee treated with the peptide of SEQ ID No. 1 as compared to placebo-treated knee was observed in most of the 17 light to heavy activities.

Further, the KOOS ADL (and WOMAC function) improvement tend to be more extensive in the group of subjects who demonstrated larger cartilage volume increase as compared to the group that cartilage volume change was negative or neutral.

These observations were within the earlier expectation that structural improvement cartilage should improve knee functions.

Knee pain was measured by KOOS pain and WOMAC pain scores.

The KOOS pain domain consists of 9 questions and each question is scored in 0-4 range. The sum of the scores, 0-36 (4×9), which is converted to a 0-100 scale to generate a KOOS pain score. While the first of the 9 questions asks for the frequency of knee pain, the other 8 questions ask for severity of knee pain during different activities or positions, where 0 is "never" experiencing pain and 4 is "always" experiencing pain. These 8 activities range from positions with little to no motion such as "at night while in bed" to those with high joint loading such as "going up or down stairs" (See FIG. 2). WOMAC pain consists of the same questions with the same scoring, except that the total score is not converted to a 100-point scale but remains in the range 0-36.

The total KOOS pain scores were very similar between the knees treated with the peptide of SEQ ID No. 1 and the placebo treated knees until 6 months after the treatment. At 12 months, the drug-treated knees showed a clinically meaningful improvement in total KOOS pain compared with placebo-exposed knees, with a trend towards statistical significance (p=0.09).

However, among the 8 statuses where the severity of knee pain was measured, only pain "going up or down stairs" showed statistically significant improvement in the knee treated with the peptide of SEQ ID No. 1 as compared to the placebo-treated knee, and the statistical significance was robust (p=0.004) (See FIG. 8).

"Going up or down stairs" is an activity that is associated with the greatest load to knee cartilage among the 8 activities of the KOOS pain score questions. The peak patella-femoral joint contact force is approximately 8 times higher during stair ascent than during walking on a level surface (Costigan, 2002).

It was surprising that the peptide of SEQ ID No. 1 significantly alleviated pain associated with only activity with the highest stress to the knee, and that it did not do so in other activities or statuses where the stress to the knee is none or less.

Further, the alleviation of pain "going up or down stairs" did not show any positive correlation with the structural change of cartilage.

This suggests that the pain alleviation by the peptide of SEQ ID No. 1 is not due to its cartilage repair activity.

As described above, it is known that the peptide of SEQ ID No. 1 does not have any anti-inflammatory or analgesic activities.

Thus, the alleviation of pain "going up or down stairs" by the peptide of SEQ ID No. 1 is for an unknown alternative mechanism triggered by administration of the peptide.

It is known that knee pain is not necessarily correlated with degree of knee cartilage destruction. There are patients who claim severe knee pain with little to no damage on their knee cartilage. On the other hand, there are severe radiographic arthritis patients with significant damage on their knee cartilage who do not feel knee pain at all.

Therefore, it is not unreasonable to determine that the pain alleviation property of the peptide of SEQ ID No. 1 is independent from its known cartilage repair activity.

The only other activity which the peptide of SEQ ID No. 1 showed near statistically significant pain alleviation was "bending knee fully" (P=0.07) (See FIG. 6). Knee bending is an activity that increases the stress on knee cartilage, though to a lesser extent than the stress associated with "going up or down stairs". It is reasonable to assume the pain on knee bending is similar, if not as severe, to that of stair climbing and descent.

The peptide of SEQ ID No. 1 did not show pain alleviation with statistical significance or trend in other activities or statuses.

In the meantime, it should be noted that the frequency of knee pain was significantly reduced by the peptide of SEQ ID No. 1. Although the peptide alleviates pain at selected activities, the patients must notice that overall frequency of pain was reduced by the treatment.

Pain going up or down stairs is one of the most common complaints by the patients whose knees are affected by osteoarthritis, rheumatoid arthritis, and knee trauma.

The unique pain alleviation property of the peptide of SEQ ID No. 1 should be highly useful to treat pain in these populations because the pain with higher stress to the knee is more difficult to control by the current most widely used pain therapeutics such as NSAIDs and acetaminophen.

Further, the peptide of SEQ ID No. 1 should alleviate pain in other joints than knee when such joints are exerted a pressure or force.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

A Randomized Double-Blind Placebo Control Study of TPX-100 in the Patients with Osteoarthritis of the Knees Clinical Study Methodology
Outline of the Study A multicenter, randomized double-blind, placebo controlled study was designed to investigate the safety, tolerability, pharmacokinetics, and efficacy of TPX-100 administered in four weekly doses in subjects with bilateral patello-femoral knee osteoarthritis. The study was conducted under an open IND (investigational new drug application) at CDER (Center for Drug Evaluation and Research) of the U.S. FDA (The United States Food and Drug Administration) in compliance with GCP (Good Clinical Practice) and ICH (International Conference on Harmonization of Technical Requirements for Registration of Pharmaceuticals for Human Use) guidelines. Eighteen (18) orthopedic, rheumatologic and family practice centers in the U.S. participated in the study.

The study was divided into Part A and Part B. The Part A was to evaluate safety of intra-articular (I.A.) administration of TPX-100 at different dosing levels (20, 50, 100, or 200 mg per injection in sequential cohorts) in the subjects with osteoarthritis of the knees and to select a dose adopted for the Part B. The Part B was to evaluate safety and efficacy of the selected dose of TPX-100.

Subjects in Part A enrolled in sequential cohorts were randomized to receive 20, 50, 100 or 200 mg of TPX-100 in one knee and identical placebo in the contralateral knee. Active and placebo assignments were randomized, with subject, site, and sponsor blinded as to treatment assignment. A Safety Review Committee (SRC) evaluated safety in each dosing cohort. The SRC assessed safety and dose-limiting toxicities, if evident, and determined whether the next higher dosing regimen might be enrolled. Part A were completed and analyzed with regard to safety prior to dose selection and initiation of Part B.

Part A included four (4) intra-articular (I.A.) injections, one per week, in sequential dosing cohorts of 20, 50, 100 and 200 mg TPX-100 versus placebo. Six (6) subjects were enrolled in 20, 50, and 100 mg cohorts, respectively, and nine (9) subjects were enrolled in 200 mg cohort. Each dosing cohort was reviewed based on safety analysis of dose groups in Part A.

The 200 mg dose was selected for Part B based on review and approval by the SRC. There were no dose-limiting toxicities for this dose or the 3 lower doses investigated in Part A. Eighty-seven (87) subjects were registered in Part B (200 mg dose) and combined with the nine subjects in the 200 mg cohort of Part A for the final drug efficacy analysis. The combined final number of the subjects that were analyzed for the drug efficacy for 200 mg dose of TPX-100 was 93.

In both Part A and Part B, subjects received 4, once-weekly doses of active drug in the knee randomized to active drug in the Index knee and placebo in the contralateral (Control) knee, delivered by the intra-articular route. No other doses of drug or placebo were administered. All subjects visited their respective clinical sites at 3, 6, and 12 months after the first dosing for their safety and efficacy assessments.

Screening of the Subjects

After informed consent was obtained, subjects underwent a clinical and laboratory screening evaluation at which their preliminary eligibility for the study was evaluated. Screening included following procedures:

Medical history including medication history
Focused physical examination
Vital signs including resting blood pressure, pulse, respiratory rate, and temperature
Weight, height, and BMI
X-ray of the knees (if not obtained within 3 months of screening)
Laboratory evaluations including hematology, coagulation profile, comprehensive metabolic panel, etc.
Recording of concomitant medications
Subjects who met all clinical and laboratory eligibility criteria underwent standardized bilateral knee MRIs.

Inclusion and Exclusion Criteria

Inclusion and exclusion criteria for screening of the subjects for either Part A or Part B were as follows:

Inclusion Criteria

1. Age ≥25 and ≤75
2. Patello-femoral osteoarthritis of both knees of mild to moderate severity with intact meniscus and ligamentous stability (cruciate and collateral ligaments)
   Clinically, as determined by screening questionnaire, judgment of the Principal Investigator (may be supporting by imaging studies of knees); confirmed by centrally read screening MRI of both knees, of ICRS Grade 1-3, or Grade 4 with only focal defects, no defect greater than 1 cm.
   Meniscus intact (MRI degenerative signal up to and including grade II acceptable)
   Cruciate and collateral ligament stability as defined by clinical examination
3. Able to read, understand, sign and date the subject informed consent
4. Willingness to use only acetaminophen as the primary analgesic (pain-relieving) study medication. The maximum dose of acetaminophen must not exceed 4 grams/day (4000 mg) per day.

5. Willingness to use only hydrocodone/acetaminophen or hydrocodone alone for breakthrough pain during the injection period (through study day 30).
6. Willingness not to use non-steroidal anti-inflammatory drugs (NSAIDS) such as aspirin, ibuprofen or naproxen for the first 30 days of the study.
7. Female subjects of child bearing potential who are sexually active (non-abstinent) must agree to and comply with using 2 highly effective methods of birth control (oral contraceptive, implant, injectable or indwelling intrauterine device, condom with spermicide, or sexual abstinence) while participating in the study.

Exclusion Criteria
1. Contraindication to MRI, including: metallic fragments, clips or devices in the brain, eye, or spinal canal; implanted devices that are magnetically programmed; weight>300 lbs.; moderate or severe claustrophobia; previous intolerance of MRI procedure
2. ICRS greater than Grade 3, excepting Grade 4 with focal defects no greater than 1 cm as confirmed by centrally-read screening MRI
3. MRI evidence of inflammatory or hypertrophic synovitis, or significant chondral calcification
4. Prior surgery in the knees, excluding procedures for debridement only
5. Knee joint replacement or any other knee surgery planned in the next 12 months
6. History of rheumatoid arthritis, psoriatic arthritis, or any other autoimmune or infectious cause for arthritis
7. Knee effusion>2+ on the following clinical scale:
   Zero=No wave produced on downstroke
   Trace=Small wave on medial side with downstroke
   1+=Larger bulge on medial side with downstroke
   2+=Effusion spontaneously returns to medial side after upstroke (no downstroke necessary)
   3+=So much fluid that it is not possible to move the effusion out of the medial aspect of the knee
8. Last viscosupplementation (e.g. Synvisc® or similar hyaluronic acid product) injected into either knee <3 months before screening
9. Last intra-articular knee injection of corticosteroids <2 months before screening
10. Use of any steroids (except inhaled corticosteroids for respiratory problems) during the previous month before screening
11. Known hypersensitivity to TPX-100
12. Known hypersensitivity to acetaminophen or hydrocodone
13. History of arthroscopy in either knee in the last 3 months before screening
14. History of septic arthritis, gout or pseudo-gout, of either knee in previous year before screening
15. Clinical signs of acute meniscal tear (e.g. locking or new acute mechanical symptoms consistent with meniscal tear)
16. Patellar chondrocalcinosis on X-Ray
17. Skin problem, rash or hypersensitivity, affecting either knee at the injection site
18. Bleeding problem, platelet or coagulation deficiency contraindicating intra-articular injection
19. Active systemic infection
20. Current treatment or treatment within the previous 2 years prior to the Screening Visit for any malignancy except basal cell or squamous cell carcinoma of the skin, unless specific written permission is provided by the Sponsor's medical monitor
21. Women of childbearing potential who are pregnant, nursing, or planning to become pregnant, and those who do not agree to remain on an acceptable method of birth control throughout the entire study period
22. Participation in other clinical osteoarthritis drug studies, with the exception of analgesic studies, within one year prior to screening
23. Currently taking Paclitaxel (mitotic inhibitor), and or Natalizumab (anti-integrin).
24. History of significant liver disease or consumption of more than 3 alcoholic drinks a day. (Definition of one alcoholic drink: 12-ounces of beer, 8-ounces of malt liquor, 5-ounces of wine, 1.5-ounces or a "shot" of 80-proof distilled spirits or liquor such as gin, rum, vodka, or whiskey).

Randomization

MRIs of both knees were evaluated by a central reader to determine the ICRS grade (gICRS) of each knee. If the cartilage of patello-femoral compartment in both knees fell within ICRS grades 1-3, or 4 with only focal defects, no defects greater than 1 cm, and all other inclusion criteria were met, with none of the exclusion criteria, the subject was registered. The randomization center randomized each subject to either Right knee active or Left knee active, with the active knee to receive TPX-100 and the contralateral knee to receive identical placebo.

For enrolled subjects, there was within-subject randomization, such that one knee received active drug injections, and the contralateral knee received identical placebo injections. Using subjects as their own control permits reduction of confounders such as weight, activity level, pain threshold, and uncharacterized genetic susceptibilities to OA progression. As two knees within a person form a matched set, the effects of individual-level confounders that are difficult to quantify (e.g. level of activity, genetic and epigenetic factors, pain threshold) are eliminated, increasing the power of the study to detect a treatment effect if one is present.

Any subject who was randomized in Part A was excluded from enrollment in Part B.

Dosing

On the first dosing day, the randomized subjects were assessed for their general health conditions by physical examinations and vital signs. Further, they completed self-reported assessments of the conditions of each of their knees as well as systemic health by the questionnaires of KOOS (Knee injury and Osteoarthritis Outcome Score), which includes subscales of WOMAC (Western Ontario and McMaster Universities Osteoarthritis Index). KOOS is a questionnaire that assesses knee-specific activities of daily living, sports and recreation function, knee-related quality of life, symptom, and knee pain. The KOOS has been used extensively in longitudinal studies of knee osteoarthritis. After these assessments, subjects received one intra-articular injection in each knee, with each injection prepared from the vial(s) marked for that knee. One knee received TPX-100, and the contralateral knee received placebo, in a triple-blind fashion (subject, site, and sponsor all blinded to treatment assignment). Subjects were monitored for adverse events during the injections and for a few hours after the injections. Vital signs were also monitored after the injections.

On the 7th, 14th, and 21st days after the first dosing, subjects received the second, third, and fourth (last) dosing of the same study materials, respectively, as well as safety and adverse event assessments in the same way as the first dosing day.

Post-Treatment Follow-Up

Subjects returned to their respective study sites at 3, 6 and 12 months after the first dosing day for follow-up evaluations. In addition, the study sites monitored the subject's condition through telephone contact 9 months after the first dosing day. During the 3, 6, and 12 months post-treatment follow-up on-site visits, subjects were evaluated by physical examination, vital signs, serum chemistry, as well as KOOS. Adverse events and concomitant medications were also recorded. Further, during the 6 and 12 month visits, MRI of both knees were taken.

Efficacy Analyses

All KOOS subscale scores were analyzed. The primary analysis was carried out using a two-sided paired t-test at the 5% level of significance. The outcome variable was the difference between the change of the score of each subscale of KOOS from baseline in the treated knee ("Index Knee") and the change from baseline in the placebo-treated knee ("Control Knee").

Results

Ninety-three (93) subjects who received 200 mg per dose of TPX-100 in one knee and placebo in contralateral knee were analyzed for efficacy.

Approximately 40% of all knees had gICRS 4 (the most severe) knee OA, all of which were in the tibio-femoral (TF) compartment, another approximately 40% had gICRS 3 (the second most severe) knee OA in both or either of patello-femoral (PF) and/or TF compartments, and the remaining approximately 20% had gICRS 2 (moderate) knee OA in both or either of PF and/or TF compartments. There were no gICRS 1 knee OA subjects. The mean body mass index (BMI) of all subjects exceeded 30, which is an obesity range. The average age of the subjects was 58.1, and 58% of the subjects were female. In summary, the demographic of the subjects in the study was very similar to that of knee OA population in the U.S., and relatively on severe side.

The TPX-100 treatments were safe and well tolerated throughout the study period. There were no severe adverse events likely or possibly related to the drug treatment. Treatment-related adverse events were mild or moderate, transient, and common in many subjects at baseline.

Several patient reported outcomes (PROs) including a majority of KOOS subscales exhibited clinically meaningful and statistically significant improvements in the Index (TPX-100 treated) knees as compared to the Control (placebo treated) knees.

The KOOS ADL (Function of Daily Living) subscale consists of 17 questions regarding various daily activities and is known to indicate day-to-day knee functions. The KOOS ADL demonstrated clinically meaningful and statistically significant ($p<0.05$) improvement in Index knees as compared to Control knees at both 6 and 12 month time points. See FIG. 12.

The KOOS Sports and Recreation subscale consists of five questions regarding harder sporting activities such as jumping, running, and squatting. The KOOS Sports and Recreation showed clinically meaningful and statistically significant improvement in Index knees as compared to Control knees at 6 months.

The KOOS knee related quality of life (QOL) subscale consists of four questions asking about the subjects' levels of confidence regarding each of their knees. The KOOS knee related QOL exhibited clinically meaningful and statistically significant improvement in Index knees as compared to Control knees at 12 months.

The KOOS Pain subscale consists of 9 questions asking 1) frequency of pain and 2) severity of pain when the subject does different activities. The KOOS Pain demonstrated clinically meaningful and statistical trend ($p<0.09$) of improvement in Index knees as compared to Control knees at 12 months.

Following are the 9 questions that consist the KOOS Pain subscale:

1. How often do you experience RIGHT/LEFT knee pain? (see FIG. 3)

Never (0), Monthly (1), Weekly (2), Daily (3), Always (4)

What amount of RIGHT/LEFT knee pain have you experienced the last week during the following activities?

None (0), Mild (1), Moderate (2), Severe (3), Extreme (4)

2. Twisting/pivoting on your knee (see FIG. 4)
3. Straightening knee fully moving (see FIG. 5)
4. Bending knee fully (see FIG. 6)
5. Walking on flat surface (see FIG. 7)
6. Going up or down stairs (see FIG. 8)
7. At night while in bed (see FIG. 9)
8. Sitting or lying (see FIG. 10)
9. Standing upright (see FIG. 11)

Analyzing severity of pain in each of these activities, improvements associated with "Going up or down stairs" (Question #6) were highly significant in Index (drug-treated) knees as compared to Control (placebo-treated) knees ($p=0.004$) at 12 months, while pain at any other activities at any time point did not show statistically significant improvements in Index knees as compared to Control knees (See Table 1). Further, the margin of pain score improvement in Index knees as compared to Control knees was outstanding in the "Going up or down stairs" as compared to that in other activities (See Table 1).

TABLE 1

Pain When Going up or down Stairs is Particularly Improved as Compared to Pain in Other Activities

| No. | Question | Score Change from Baseline to 12 Months | | | |
|---|---|---|---|---|---|
| | | Index | Control | Difference | p-value |
| 1 | How often do you experience RIGHT/LEFT knee pain? | −0.62 | −0.37 | −0.26 | 0.04 |
| | What amount of RIGHT/LEFT knee pain have you experienced last week during the following activities? | | | | |
| 2 | Twisting/pivoting on your knee | −0.19 | −0.11 | −0.09 | 0.52 |
| 3 | Straightening knee fully moving | −0.30 | −0.18 | −0.12 | 0.27 |
| 4 | Bending knee fully | −0.45 | −0.22 | −0.24 | 0.07 |
| 5 | Walking on flat surface | −0.25 | −0.13 | −0.12 | 0.29 |
| 6 | Going up or down stairs | −0.51 | −0.17 | −0.33 | 0.004 |
| 7 | At night while in bed | −0.19 | −0.19 | 0.00 | 1.00 |
| 8 | Sitting or lying | −0.26 | −0.24 | −0.02 | 0.84 |
| 9 | Standing upright | −0.34 | −0.18 | −0.16 | 0.15 |

[Notes]
1) Index = TPX-100 treated knees; Control = Placebo treated knees.
2) Neither subjects nor caregivers knew which knee (RIGHT/LEFT) received TPX-100 or Placebo throughout the entire study period.
3) Negative score change means frequency (for Question 1) or severity (for Questions 2-9) of pain was decreased.
4) Difference = [Index score change] − [Control score change]. More negative number means more improvement in Index knee as compared to Control.
5) Among eight different activities (Questions 2-9), Going up or down stairs (Question 6) was the only activity that showed statistically significant ($p<0.05$) pain reduction in Index knees as compared to Control, and the degree of significance was outstanding.
6) Overall frequency of knee pain (Question 1) also showed statistically significant improvement in Index knees as compared to Control.

The observed improvements in knee functions and overall knee health conditions as demonstrated by KOOS ADL, KOOS Sports & Recreation, and KOOS Knee-related QOL were reasonably predicted from knee cartilage repair activities demonstrated in the prior non-clinical (goat model) studies (See U.S. Pat. No. 8,426,558), because, theoretically, regeneration of healthy cartilage should make the knee joint movement smoother.

On the other hand, the observed significant improvement in pain was unexpected. First, cartilage contains no nerve supply, therefore, cartilage repair or regeneration would not affect pain scores. Second, TPX-100 does not have any analgesic or anti-inflammatory activities.

Among the eight activities (#2-9) making up the KOOS Pain score, "Going up or down stairs" involves a patella-femoral joint contact force approximately 8 times higher during stair ascent than during walking on a level surface (Costigan Pa., 2002). It was surprising and unexpected finding that TPX-100 treatment improved pain scores in the activity associated with greatest patella-femoral cartilage stress among the eight activities making up the KOOS pain score. Only pain at "Bending knee fully" showed a trend ($p<0.09$) of improvement.

Knee pain at going up or down stairs is one of the most common complaints that rheumatologists, orthopedists, and sports medicine doctors hear from their patients in association with cartilage disease, whether from OA, rheumatoid arthritis, or joint trauma. In addition, this knee pain has been found to be among the earliest signs of knee osteoarthritis (Hensor E M, 2015). This particular result suggests that TPX-100 may be useful treating knee pain when going up or down stairs, regardless of the pathology of such knee pain.

Also, it should be noted that frequency of overall knee pain (Question #1) was significantly improved ($p=0.04$) in Index knees compared with Control knees at 12 months. This suggests that improvement in pain "Going up or down stairs" contributes substantially to overall pain in knee osteoarthritis.

Thus, TPX-100 presents a new method to treat pain in the knee in arthritic or other pathologic or traumatic conditions by alleviating the pain when going up or down stairs.

REFERENCES

Bedson and Croft, BMC Musculoskeletal Disorders 2008, 9:116 doi: 10.1186/1471-2474-9-116
Buckwalter J A. Articular cartilage injuries. Clin Orthop Relat Res 2002; 21-37
Chevalier X, et al. Single, intra-articular treatment with 6 cc hylan G-F 20 in subjects with symptomatic primary osteoarthritis of the knee: a randomized, multi-centre, double-blind, placebo controlled trial. *Ann Rheum Dis* 2010; 69: 113-119.
Cohen M D. Hyaluronic acid treatment (viscosupplementation) for OA of the knee. *Bull Rheum Dis.* 1998; 47; 4-7.
Costigan P A, Deluzio K J, Wyss U P. Knee and hip kinetics during normal stair climbing. *Gait Posture.* 2002 August; 16(1):31-7.
Davies A P. The Radiologic Prevalence of Patellofemoral Osteoarthritis. *Clinical Orthopaedics and Related Research.* 2002; 402; 206-212
Hensor E M, Dube B, Kingsbury S R, Tennant A, Conaghan P G. Toward a Clinical Definition of Early Osteoarthritis: Onset of Patient-Reported Knee Pain Begins on Stairs. Data from the Osteoarthritis Initiative. *Arthritis Care Res (Hoboken).* 2015 January; 67(1):40-7. doi: 10.1002/acr.22418
Lankhorst N E, et. al. Incidence, Prevalence, Natural Course and Prognosis of Patellofemoral Osteoarthritis: the Cohort Hip and Cohort Knee Study, *Osteoarthritis and Cartilage.* 2017; 25(5):647-653
McAlindon T E, et. al. Effect of Intra-articular Triamcinolone vs Saline on Knee Cartilage Volume and Pain in Patients with Knee Osteoarthritis, A Randomized Clinical Trial. *JAMA* 2017; 319(19):1967-1975.doi:10.1001/jama.2017.5283
Niemeyer M D, et al. Characteristic Complications After Autologous Chondrocyte Implantation for Cartilage Defects of the Knee Joint. Am J Sports Med 2008: 36:2091-2099
Woolf A D, Pfleger B, Burden of major musculoskeletal conditions. Bulletin of the World Health Organization 2003; 81 (9): 646-56.
Zaslav K, et al. A prospective study of autologous chondrocyte implantation in subjects with failed prior treatment for articular cartilage defect of the knee: Results of the Study of the Treatment of Articular Repair (STAR) clinical trial. Am J Sports Med. 2009; 37:42-55.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for reducing the frequency of overall joint pain experienced by a subject, comprising:
    injecting a joint of the subject with the injectable aqueous formulation comprising an amino acid sequence TDLQERGDNDISPFSGDGQPFKD (SEQ ID NO: 1)
    evaluating joint pain in the subject after administering the formulation,
    whereby the formulation reduces joint pain in the subject.

2. The method of claim 1, where the joint is a knee joint.

3. The method of claim 1, wherein the injection is intra-articular in a dosage range of 100-400 mg.

4. The method of claim 1, wherein the peptide of SEQ ID NO: 1 is administered in combination with hyaluronic acid.

5. The method of claim 3, wherein the peptide is administered in a dose of 200 mg and administered once a week for 3 weeks.

6. The method of claim 1,
    wherein the subject as experiencing joint pain when the patient is undergoing an activity which stresses the joint.

7. The method of claim 6, where the activity which stresses the joint is a greater degree of knee bending than necessary to walk on a flat surface.

8. The method of claim 7, where the activity is going up or down stairs.

9. The method of claim 1, where the subject suffers from at least one of osteoarthritis, rheumatoid arthritis, or joint trauma in the joint with the pain.

10. The method of claim 1, wherein the subject experiences pain less frequently going up or down stairs after the injecting.

11. The method of claim 10, wherein the peptide of SEQ ID NO: 1 is administered in combination with hyaluronic acid; and
    wherein the peptide is administered in a dose in a range of 100 mg to 400 mg per one injection and administered once per week for three weeks.

* * * * *

SEQUENCE LISTING

```
<160> NUMBER OF SEQ ID NOS: 1

<210> SEQ ID NO 1
<211> LENGTH: 23
<212> TYPE: PRT
<213> ORGANISM: Artificial sequence
<220> FEATURE:
<223> OTHER INFORMATION: Synthetic peptide sequence

<400> SEQUENCE: 1
```

```
Thr Asp Leu Gln Glu Arg Gly Asp Asn Asp Ile Ser Pro Phe Ser Gly
1               5                   10                  15

Asp Gly Gln Pro Phe Lys Asp
            20
```